United States Patent [19]
Gold

[11] Patent Number: 5,407,813
[45] Date of Patent: Apr. 18, 1995

[54] PREPARATION OF NUCLEIC ACID DELETION FRAGMENTS

[75] Inventor: Paul Gold, St. Louis, Mo.

[73] Assignee: Gold Biotechnology, St. Louis, Mo.

[21] Appl. No.: 517,320

[22] Filed: May 1, 1990

[51] Int. Cl.[6] .................. C12P 19/34; C12Q 1/68; C07H 21/04; C12N 15/00

[52] U.S. Cl. .................. 435/91.2; 435/6; 536/24.33; 935/77; 935/78

[58] Field of Search .............. 435/6, 91.2; 536/27, 536/24.33; 935/77, 78

[56] References Cited

U.S. PATENT DOCUMENTS 4,683,202  7/1987  Mullis ............................ 435/91

OTHER PUBLICATIONS

Sambrook et al., "Molecular Cloning" Second Edition, Cold Spring Harbor Laboratory Press 1989, pp. 8.49; 11.9–11.10; 11.45–11.61; 14.2–14.35.
Sanger et al., "DNA Sequencing with Chain-terminating Inhibitors", Proc. Natl. Acad. Sci. USA, vol. 74, No. 12, pp. 5463–5467, Dec. 1977.
Maxam et al., "A New Method For Sequencing DNA", Proc. Natl. Acad. Sci. USA, vol. 74, No. 2, pp. 560–564, Feb. 1977.
Henikoff, "Unidirectional Digestion with Exonuclease III in DNA Sequence Analysis", Methods in Enzymology, vol. 155, pp. 156–165.
Henikoff, "Unidirectional Digestion with Exonuclease II Creates Targeted Breakpoints for DNA Sequencing", Gene, vol. 28, pp. 351–359, 1984.
Sorge et al., "ExoMeth Sequencing of DNA: Eliminating the Need for Subcloning and Oligonucleotide Primers", Proc. Natl. Acad. Sci. USA, vol. 86, pp. 9208–9212, Dec. 1989.
Mazzarella et al., "ERp99, an Abundant, Conserved Glycoprotein of the Endoplasmic Reticulum . . . ", Journal of Bio. Chem., vol. 262, No. 18, pp. 8875–8883, Jun. 25, 1987.
Orlandi et al., "Cloning Immunoglobulin Variable Domains for Expression by the Polymerase Chain Reaction", Proc. Natl. Acad. Sci. USA, vol. 86, pp. 3833–3837, May 1989.
Sastry et al., "Cloning of the Immunological Repertoire in *Escherichia Coli* for Generation of Monoclonal Catalytic Antibodies: Construction of A Heavy Chain Variable Region-Specific cDNA Library", Proc. Natl. Acad. Sci. USA, vol. 86, pp. 5728–5732, Aug. 1989.
Gorman et al., "Simplified Method for Selective Amplification and Direct Sequencing of cDNAs", BioTechniques, vol. 7, No. 4, pp. 326–329, 1989.
Rychlik et al., "A Computer Program for Choosing Optimal Oligonucleotides for Filter Hybridization, Sequencing and in Vitro Amplification of DNA", Nucleic Acids Research, IRL Press, vol. 17, No. 21, 1989.
"Agarose Gel Electrophoresis", pp. 150–163.
"The ExoMeth ™ Sequencing Kit", Stratagene, 5 pages.

*Primary Examiner*—Mindy B. Fleisher
*Attorney, Agent, or Firm*—Senniger, Powers, Leavitt & Roedel

[57] ABSTRACT

Process for the preparation of a deletion fragment from a target nucleic acid, the target having a region of known nucleotide sequence identical to one terminus of the deletion fragment. In the process, the target nucleic acid is provided as a single stranded molecule. A terminus primer which is homologous to the region of known nucleotide sequence, and a set of deletion primers each of which has a fixed site region, a spacer region and a tail are also provided. The set of deletion primers contain a mixture of oligonucleotides which have homologous fixed site regions and homologous tails, and which collectively have all four bases at each nucleotide position in essentially all combinations thereof in their spacer regions. The single strands are treated with the terminus primer and the set of deletion primers to form a primer extension product wherein the target nucleic acid is used as a template.

37 Claims, 2 Drawing Sheets

PREPARATION OF NUCLEIC ACID DELETION FRAGMENTS

This invention was made with Government support under NIH Grant #DK 40266-03 awarded by the National Institutes of Health. The Government has certain rights in the invention.

The present invention relates to a process for the preparation of deletion fragments of a nucleic acid template, the process having utility in confirming the sequence of mutagenic DNA and in the sequencing of a nucleic acid template.

Currently, the length of target DNA that can be sequenced accurately in a single set of sequencing reactions is typically about 400 bases. Target DNAs of this length can be directly sequenced using the enzymatic method of Sanger et al., Proc. Natl, Acad. Sci. 74:5463 (1977), or the chemical degradation method of Maxam and Gilbert, Proc, Natl. Acad. Sci. 74:560 (1977).

However, many applications require accurate nucleotide sequence information for previously unresolved segments of DNA that may be many kilobases in length. To date, at least two strategies have been developed in an effort to sequence DNA of this length. The first is a random approach in which sequence data are collected from subclones containing random segments of the target DNA. No attempt is made to determine where these subclones map in the target DNA or which strand of DNA is being sequenced. Instead, the accumulated data are stored and finally arranged in order by a computer. While this approach has been used successfully to determine the sequences of certain target DNAs, its utility is limited because of the need for access to adequate computing facilities. Also, because subclones are selected at random, certain regions of the target DNA will be sequenced repeatedly before the entire region is covered, and there is no way to predict how long it will take to find and sequence the last subclones required to complete a sequence. Often these subclones turn out to be underrepresented in the library, and it is then necessary to isolate them by screening with oligonucleotide probes corresponding to flanking sequences.

The other principal strategy developed for accurately determining sequence information for target DNAs of many kilobases in length is a directed approach in which sequences of the target DNA are obtained by sequencing a nested set of deletion fragments that begin at a common point (typically at one end of the target DNA) and penetrate various distances into the target region. The deletion fragments thus bring progressively more remote regions of the target DNA into range for sequencing.

Several strategies have been proposed for generating a nested set of deletion fragments for use in sequencing. By far the most popular is the one described by Henikoff in Gene 28:351 (1984) and Methods Enzymol. 155:156 (1987) in which unidirectional deletion mutants are created by digesting double-stranded DNA with two restriction enzymes whose sites of cleavage both lie between one end of the target DNA and the primer-binding site. The enzyme that cleaves nearer the target sequences must generate a blunt end or a recessed 3' terminus; the other enzyme must generate a 3- or 4-nucleotide protruding 3' terminus. Because only one end of the resulting linear DNA is susceptible to exonuclease III, digestion proceeds unidirectionally away from the site of cleavage into the target DNA sequences. The exposed single strands are removed by digestion with an appropriate nuclease. The DNA is then recircularized and used to transform bacteria. After transformation, the resulting clones are analyzed in order to assemble a nested set.

Although the Henikoff method yields accurate results, it does, nevertheless, suffer from several limitations. Some investigators have reported that exonuclease III digests at different rates through the target DNA depending upon its A-T or G-C content. Such variances in rate may result in gaps in the resulting mutants because an investigator would not know how to vary the time points in order to capture a representative nested set with an unknown DNA sequence. In addition, many of the steps are labor intensive and require the services of a skilled technician.

Another method for generating a nested set of deletion fragments has recently been proposed by Sorge et al. in Proc. Natl. Acad. Sci. 86:9208 (1989). According to the Sorge et al. method, exonuclease III is used to directionally digest the DNA and aliquots are removed at timed intervals. Dideoxy sequencing reactions are then performed in the presence of methylated dCTP which will inhibit subsequent restriction in the newly synthesized strand. However, the original template is still susceptible to cleavage and the DNA is digested with restriction enzyme sensitive to methyl dCTP in its recognition site. The molecules at each time point will theoretically have the same end point, thereby allowing reading of the sequence within the separation parameters of the sequencing gel.

Although the Sorge et al. method overcomes several of the limitations associated with the Henikoff method, e.g., the need to subclone and isolate a nested set of deletion mutations and the need for sequencing primers, it suffers from other limitations. According to the manufacturer of a commercial kit which employs the Sorge et al. method (Stratagene; La Jolla, Calif.), the method requires a large amount of DNA (about 270 µg) free of nicks to sequence 5 kilobases. In addition, because exonuclease III endpoints will vary about +/−4% of the nucleotides deleted, as the digestion proceeds, the distribution of endpoints increases. At larger deletions this increase in distribution can become a problem because of the subsequent restriction digestion. If the range of endpoints becomes too great, the template will encompass more than one restriction site for a given enzyme. As a result, the sequencing gel would not be readable because of the presence of two overlapping sequencing ladders. The DNA from unreadable time points must then be redigested using another enzyme whose site has been discovered in the initial analysis. Since both strands are being sequenced, it is likely that one can obtain different information from the other strand and more sequencing gels must then be run for unreadable time points for this strand. Furthermore, it is important to confirm the sequence data by sequencing each strand. In conclusion, the Sorge et al. method is an advance, but is still quite labor intensive.

For some years now and for a variety of reasons, researchers have attempted to cause the mutation of certain regions of a native DNA sequence and then incorporate the mutagenic DNA into a gene. This mutagenic DNA typically differs from the native DNA in at least one nucleotide position.

Regardless of how the mutation is created, the researcher must often unambiguously show that the newly mutated gene is of the desired sequence. If there is a convenient restriction site near the mutagenized region (within about 200–300 bases), a fragment of the mutant gene may be cloned. Subsequent sequencing analysis can be performed using a primer which hybridizes to a region of the vector DNA close enough to the mutagenized region to allow verification of the sequence. For example, if the mutant fragment was cloned into the popular M13 vectors, the M13 forward or M13 reverse primer can be used for sequencing. However, if there are no convenient restriction sites, an alternative procedure must be used. In one such alternative method for sequencing the mutagenized region, an oligonucleotide which is complementary to the DNA 5' or 3' to the mutagenized region is synthesized and purified, and then used as a sequencing primer. Although this is an effective method to confirm the sequence of the mutagenized DNA, it can be unduly costly and the presence of secondary structure in the oligonucleotide may prevent its use as an effective sequencing primer.

SUMMARY OF THE INVENTION

Among the objects of the invention, therefore, may be noted the provision of a process for the preparation of a deletion fragment from a target nucleic acid, the provision of a such process which may be used to produce a nested set of fragments from a target nucleic acid, the provision of such a process which does not require restriction mapping, preparing subfragments for subcloning, identifying subclones, or growing bacterial cultures, the provision of such a process which does not require a relatively large quantity of target nucleic acid, the provision of such a process which does not require a timed incubation of the nucleic acid with an enzyme accompanied by the removal of aliquots at predetermined time points, the provision of such a process that is less labor intensive than preexisting processes, a process which reduces the number of steps requiring a skilled technician, and the provision of such a process which may be used to confirm the sequence of mutagenic DNA.

Briefly, therefore, the present invention is directed to a process for the preparation of a deletion fragment from a target nucleic acid, the target nucleic acid having a region of known nucleotide sequence which is identical to one terminus of the deletion fragment. The process comprises providing the target nucleic acid as a single stranded molecule, providing a terminus primer which is homologous to the region of known nucleotide sequence, and providing a set of deletion primers which have a fixed site region, a spacer region and a tail. Each set of deletion primers comprises a mixture of oligonucleotides which have homologous fixed site regions and homologous tails, the spacer region comprising N consecutive nucleotide positions wherein N is at leash two, the mixture comprising about $4^N$ oligonucleotides. According to the process, the target nucleic acid is treated with the terminus primer and the set of deletion primers in the presence of an inducing agent to form a primer extension product using the target nucleic acid as a template. The primer extension product(s) resulting from such treatment step are separated from the templates on which they were synthesized to produce single stranded molecules, and the single stranded molecules are then used as a template for the formation of additional primer extension products. Such cycling may be repeated as many times as desired.

The present invention is also directed to a kit for the preparation of a nested set of deletion fragments from a target nucleic acid. The kit comprises a plurality of sets of deletion primers having a fixed site region, a spacer region and a tail. Each set of primers comprises a mixture of oligonucleotides which have homologous fixed site regions and homologous tails and which collectively have all four bases at each nucleotide position in essentially all combinations thereof in their spacer regions. Distinct sets of primers differ from one another with respect to the sequence of bases which comprise the fixed site regions of their respective mixtures.

The present invention is further directed to a mixture of oligonucleotide primers having a fixed site region, a spacer region and a tail, with each region independently comprising a predetermined number of nucleotides. The oligonucleotides have homologous fixed site regions and homologous tails. Collectively, the oligonucleotides have all four bases at each nucleotide position in essentially all combinations thereof in their spacer regions.

Other objects will be in part apparent and in part pointed out hereinafter.

DETAILED DESCRIPTION OF THE PREFERRED EMBODIMENTS

The term primer as used herein refers to an oligonucleotide, whether occurring naturally as in a purified restriction digest or produced synthetically, which is capable of acting as a point of initiation of synthesis when placed under conditions in which synthesis of a primer extension product commences. The exact length of the primers will depend on many factors, but typically contains between about 10 and 30 nucleotides.

The term inducing agent as used herein shall mean any compound or system which will function to accomplish the synthesis of primer extension products, including enzymes which are disclosed, for example, in Mullis U.S. Pat. No. 4,683,202 at col. 7, line 69 et seq. A particularly preferred enzyme is the Taq polymerase.

The polymerase chain reaction (PCR) has been used to amplify a segment of DNA that lies between two regions of known sequence. PCR is based on the use of two oligonucleotides to prime DNA polymerase-catalyzed synthesis from the opposite strands across a region spanned by the priming sites of the two oligonucleotides. By repeated cycles of denaturation of the DNA strands, annealing of oligonucleotide primers, and DNA synthesis in the presence of an inducing agent, an exponential increase of a discrete DNA fragment can be achieved. See, e.g., Mullis et al. U.S. Pat. No. 4,683,202 which is incorporated herein by reference.

Surprisingly, it has been discovered that a deletion fragment containing a specific nucleic acid sequence from a target nucleic acid can be prepared and amplified by using a set of deletion primers and a terminus primer of the present invention in a PCR process. Such a fragment has utility in the sequencing of unknown regions of DNA when the deletion fragment is prepared as one of a nested set of deletion fragments and in confirming the sequence of mutagenic DNA.

Where the target nucleic acid consists of two complementary strands, the terminus primer is selected to be substantially identical to a region of known sequence at the 5' terminus (of either strand) of the region for which the fragment is desired. Where the target nucleic acid is a single stranded molecule, the terminus primer is selected to be substantially identical to a region of known sequence at the 5' terminus of the region for which the fragment is desired.

The deletion primers comprise oligonucleotides having three regions: a fixed site region, a spacer region and a tail. Each region comprises a predetermined number of nucleotides with the fixed site region being at the 3' end of the oligonucleotide, the tail being at the 5' end of the oligonucleotide and the spacer region being in between.

Preferably, the fixed site region comprises between about 5 and 7 consecutive bases, and most preferably 6 consecutive bases. The fixed site region (located at the 3' end of the primer) is designed to hybridize to the target nucleic acid and serve as the primer from which chain extension proceeds in the presence of an inducing agent.

The tail at the 5' end of the deletion primer preferably comprises at least about 20 bases and has the characteristics of a good sequencing primer. Although all such characteristics have not been fully defined, it is currently believed that such characteristics include limited self-complementarity, low secondary structure, high melting temperature, and sufficient G+C composition. See, e.g., Guide to DNA sequencing, EG&G Biomolecular, 1989, Natick, Mass., and Rychlik & Rhoads, *Nucleic Acids Research* 17:8543–8551 (1989). In the first round of amplification, the tail preferably does not strongly hybridize to the target DNA. In subsequent rounds of amplification the tail is incorporated into the amplified DNA. Thus, after two rounds of amplification the entire deletion primer (both 3' end and 5' tail) can hybridize to the amplified DNA.

The spacer region comprises at least about 2 consecutive nucleotide positions, preferably between about 4 and about 10 consecutive nucleotide positions, and most preferably 6 consecutive nucleotide postions. Like the fixed site region, the spacer region is designed to interact with the target nucleic acid and assist in "holding" the primer to the target nucleic acid for primer extension.

For use in the process of the present invention, the deletion primers are provided in sets. Each set of deletion primers is a mixture of oligonucleotides sharing the same sequence of bases in their fixed site regions and tails, but having different sequences of bases in their respective spacer regions. More specifically, the oligonucleotides of a single set collectively have each base represented at each nucleotide position within the spacer region in essentially all combinations thereof. Thus, each deletion primer set is a mixture of about $4^N$ oligonucleotides where N equals the predetermined number of nucleotides comprising the spacer region. By way of example, therefore, if the spacer comprises one nucleotide (N=1) a single deletion primer set will comprise four oligonucleotides which have A, C, G, and T appearing, respectively, in the spacer region nucleotide position. By way of further example, if the spacer comprises two nucleotides (N=2) a single deletion primer set will comprise sixteen oligonucleotides which have AA, AC, AG, AT, CA, CC, CG, CT, GA, GC, GG, GT, TA, TC, TG, and TT appearing, respectively, in the spacer region nucleotide positions.

Whereas each set of deletion primers is a mixture of oligonucleotides having the same sequence of bases in their fixed site regions and tails but different sequences of bases for their respective spacer regions, deletion primers of distinct sets differ from one another with respect to the sequence of bases comprising their respective fixed site regions. That is, the oligonucleotides of distinct sets of deletion primers have a different sequence of bases comprising their respective fixed site regions. By way of example, the mixture of oligonucleotides comprising a first set of deletion primers could have the sequence CCCCTT and the mixture of oligonucleotides comprising a second set of deletion primers could have the sequence CCTTTT.

Because it is the fixed site region which is primarily responsible for the interaction between the deletion primer and a target nucleic acid, different sets of deletion primers have the potential to hybridize with a different portion of the target nucleic acid and produce unique deletion fragments. Accordingly, it is possible to generate a nested set of deletion fragments by treating separate aliquots of the target nucleic acid with the different sets of deletion primers, i.e., adding one deletion primer set per aliquot, and then amplifying any fragments produced thereby.

Figure 1:
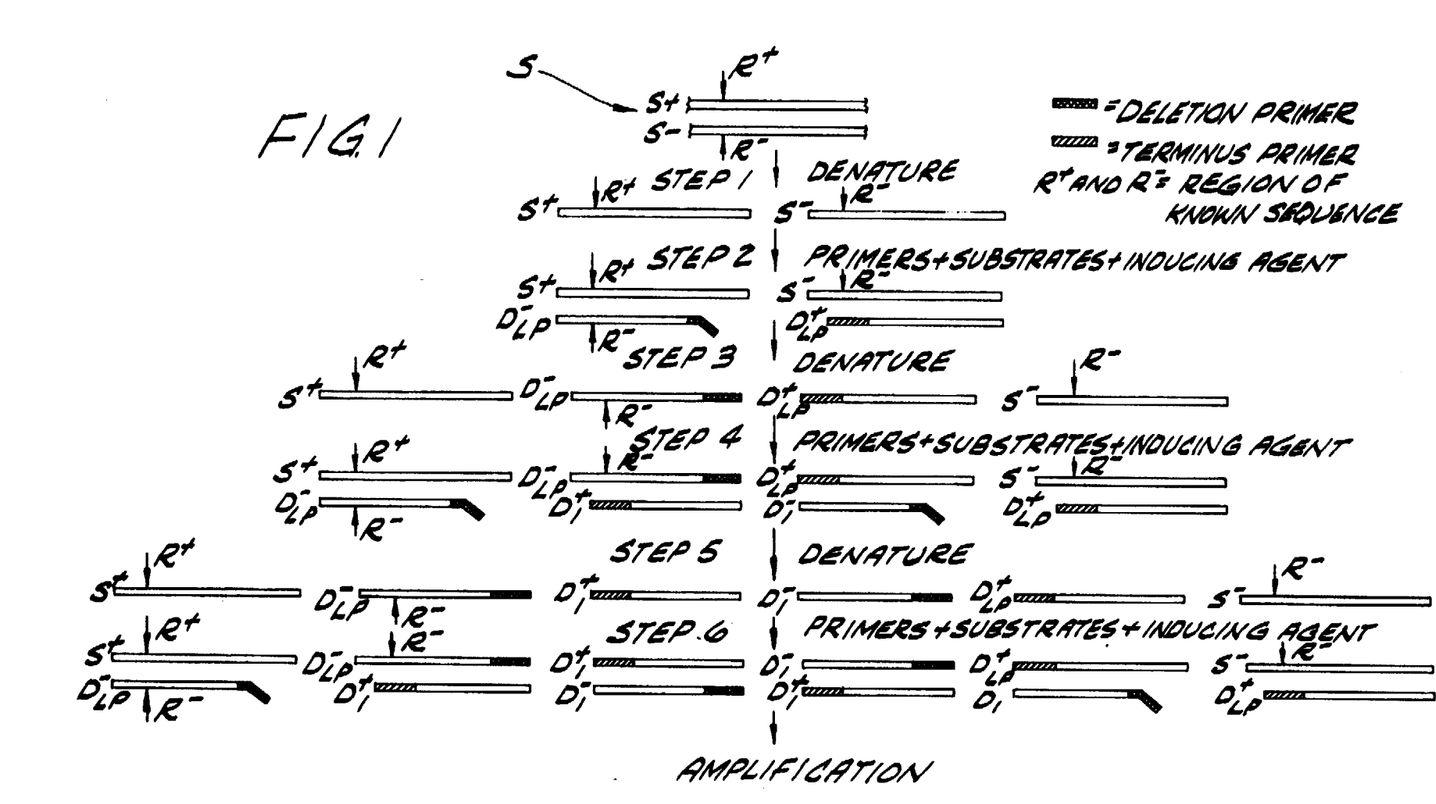
FIG. 1 is a schematic representation of one embodiment of the process of the present invention.

The preparation and amplification of a deletion fragment in accordance with the process of the present invention is depicted in FIG. 1. Double stranded DNA containing the desired fragment S comprised of complementary strands S+ and S− is utilized as the target nucleic acid. Strands S+ and S− have a region of known sequence R+ and R−, respectively. For purposes of this explanation only, the terminus primer selected is identical to the region of known sequence of the (+) strand; in actual studies the terminus primer could be identical to either the (+) or (−) strand. In step 1, the double stranded DNA is denatured, for instance, by melting at 94° C. In step 2, the separated strands are treated with a terminus primer homologous to the region of known sequence R+, a set of deletion primers of the present invention, substrates (deoxyribonucleoside triphosphates) and an inducing agent under conditions conducive to the formation of a primer extension product. The deletion primer will hybridize with strand S+ and undergo chain extension to form a long product deletion fragment $D^-_{LP}$ using strand S+ as a template, and the terminus primer will hybridize with strand S− and undergo chain extension to form a second long product deletion fragment $D^+_{LP}$. In step 3, the double stranded molecules produced in step 2 are denatured to produce single stranded S+, $D^-_{LP}$, $D^+_{LP}$, and S− molecules In step 4, these single stranded molecules are subjected to conditions conducive to the formation of a primer extension product in the presence of the terminus primer, deletion primers and inducing agent. The deletion primer will hybridize with S+ and $D^+_{LP}$ and undergo chain extension to form a second copy of long product deletion fragment $D^-_{LP}$ and the desired deletion fragment $D_1^-$, respectively. The terminus primer will hybridize with strands S− and $D^-_{LP}$ and undergo chain extension to form a second copy of long product deletion fragment $D^+_{LP}$ and the desired deletion fragment $D_1^+$, respectively. In step 5, the double stranded molecules produced in step 4 are denatured to produce single stranded S+, $D^-_{LP}$, $D_1^+$, $D_1^-$, $D^+_{LP}$ and S− molecules. Repeating the hybridization and denaturing steps will result in exponential amplification of strands $D_1^+$ and $D_1^-$, and arithmetic growth in strands $D^-{}_{LP}$ and $D^+{}_{LP}$. In this schematic representation, it was assumed that the deletion primer only hybridized with the template at one site. In practice, the deletion primer may hybridize with the template at a plurality of sites in which case, the amplification process would produce products $D^+{}_{1-i}$ and $D^-{}_{1-i}$ where i equals the number of sites of hybridization.

When the process of the present invention is used to prepare a nested set of deletion fragments, it is preferred that the deletion fragments not be separated by more than about 400 bases, and most preferably are not separated by more than about 160 bases. The distance between the deletion fragments is affected to a great extent by the selection of a predetermined number of sets of deletion primers used to generate the deletion fragments and the predetermined number of bases comprising the fixed site region.

The selection of a predetermined number of bases for the fixed site region requires balancing two considerations. First, the 3' end of the deletion primer must be of sufficient length to stably interact with the target nucleic acid. Second, it must also be short enough so that a manageable number of sets of deletion primers may be used to generate a series of overlapping deletion fragments separated by a length which permits sequencing. For instance, if the target nucleic sequence were completely random, a five base region occurs on average every 1,024 bases ($4^5$) and 7 sets of primers having different five base regions would be required to generate deletion fragments separated on average by about 160 bases (1,024/7) Likewise, a six base region would occur on average every 4,096 bases in a completely random nucleic acid sequence and about 25 sets of primers having different six base regions would be required to generate deletion fragments separated on average by about 160 bases (4,096/25). By way of further example, a seven base region would occur on average every 16,384 bases in a completely random nucleic acid sequence and about 100 sets of primers having different seven base regions would be required to generate deletion fragments separated on average by about 160 bases (16,384/100). As between a five, six or seven base region, therefore, a five base region would allow for the use of a relatively low number of sets of deletion primers (7), but in experimental runs working with a known target DNA sequence to date a five base fixed site region has generated a few fragments but not nearly the expected number. Conversely, in comparable experiments with a seven base fixed site region most of the expected fragments were generated, but it is impractical for a researcher to work with 100 or more different sets of deletion primers. Accordingly, a six base fixed site region appears to be the best compromise; experience has shown that a six base fixed site region generates most of the expected fragments, and the number of sets of deletion primers with which a researcher must work (25 if nucleic acids were completely random in sequence) is practical.

In practice, target nucleic acid sequences are not completely random; some sequences occur with a greater frequency than mathematical probabilities alone would suggest and others occur with less frequency. Thus, it is preferred that the number of sets of deletion primers used to generate deletion fragments separated by about 160 bases for a fixed site primer of a predetermined length be greater than that which would be used for a completely random sequence. For instance, for a six base fixed site region it is preferred to use about 35 sets of deletion primers instead of 25. Therefore, for a seven base fixed site region it would be preferred to use about 140 sets of deletion primers instead of 100.

The sequences for the fixed site region of a set of deletion primers may be selected based upon information concerning the frequency of appearance of certain sequences in a DNA library for the species in which the target DNA appears. For example, GenBank/Intelligenetics (Mountain View, Calif.) is a depository of DNA sequence data for all species and currently is the leading source of sequence information. It is regularly used and updated by researchers working in the field. The frequency of appearance information can thus be obtained by analyzing the frequency with which predetermined sequences appear in the DNA library. Accordingly, a number of those sequences which occur at a frequency greater than that which would be expected based upon mathematical probabilities alone (assuming that DNA sequence is completely random) are selected for use as fixed site regions. The frequency of certain fixed site regions in genes will be a reflection of codon frequency.

As noted above, the spacer region is designed to interact with the target nucleic acid and assist in "holding" the primer to the target nucleic acid for primer extension. Thus, the length of the spacer region has some effect upon the stability of any hybrids formed between the deletion primer and the target nucleic acid.

In general, the length of the fixed site and spacer regions are related. Preferably, the combined total of nucleotides comprising the fixed site and spacer regions in the deletion primers is at least about 9. More preferably, the combined total is at least about 10 and most preferably at least about 12 nucleotides.

With a six base spacer, the degeneracy of the oligonucleotides within a set is 1/4096 ($4^6$); that is, only one out of every 4096 oligonucleotides in the set is identical. However, the concentration of primers during the initial rounds in the amplification process is so high that the degeneracy does not appear to matter. In subsequent rounds of amplification when the primer concentration drops, all of the oligonucleotides present in the mixture will share identical 5' (the tail) and 3' (fixed site region) termini. Only the spacer region will be unique to each oligonucleotide. Without being bound to any specific theory, therefore, it is believed that a heteroduplex is formed in these subsequent rounds of amplification between a slightly mismatched primer and template.

Any source of nucelic acid, in purified or nonpurified form, can be utilized as the starting target nucleic acid. Thus, the process may employ, DNA or RNA, including messenger RNA. The DNA and RNA may be single or double stranded. If the nucleic acid is double stranded, it is necessary to separate the strands before it can be used as a template. In addition, if the nucleic acid is RNA, cDNA should be synthesized for use as the template.

The target nucleic acids may be obtained from any source, for example, from plasmids, from cloned DNA or RNA, or from natural DNA or RNA from any source including bacteria, yeast, viruses, and higher organisms such as plants or animals. Preferably, the nucelic acid is isolated from a PCR generated target fragment via agarose gel followed by differential binding to a silica matrix, which is commercially available from Bio 101 Inc. (La Jolla, Calif.) under the trademark Gene-Clean.

To prepare a nested set of deletion fragments, the target nucleic acid is provided as a single stranded molecule and divided into separate aliquots, preferably of at least about 5 nanograms ($2.5 \times 10^{-15}$ moles) for a 3,000 base pair fragment per aliquot. To each aliquot are added a set of deletion primers, the terminus primer, an inducing agent and the deoxyribonucleoside triphosphates. Preferably one set of deletion primers and one terminus primer are added per aliquot, with the aliquots collectively being treated with a plurality of deletion primer sets to generate a nested set of fragments. The treated aliquots are subjected to conditions conducive for the formation of primer extension products using the target nucleic acid as a template. The newly synthesized strand and its complementary strand form a double-stranded molecule which is used in the succeeding steps of the process. Further cycling will result in the amplification of different deletion fragments from the various aliquots.

During the PCR cycling steps of the present invention, it is preferred that the denaturation step be carried out at about 94° C. for two minutes, that the hybridization step be carried out at about 42° C. for two minutes and that the polymerization step be carried out for about four minutes with Taq polymerase at about 72° C. To date, performing the hybridization at about 42° C. appears to be optimal for deletion primers comprising a six-nucleotide fixed site region and a six-nucleotide spacer region; performing the hybridization at 47° C. results in decreased efficiency, and at 52° C. even less PCR products are seen.

Upon completion of the PCR amplifications, the DNA fragments are sequenced using standard technique. A suitable protocol is outlined in Gorman et al., Biotechniques 7:326–329 (1989) which is incorporated herein by reference. Preferably, the DNA fragment to be sequenced is first isolated by gel electrophoresis. The band is then cut out without further purification. The sequencing reactions are then carried out in the presence of agarose, preferably GTG seaplaque sold by FMC (Rockland, Me.), which is a high quality non-inhibitory low melting agarose.

The kits of the present invention contain a plurality of sets of deletion primers. The number of sets of deletion primers is preferably such that the primers, are likely, based upon statistics, to hybridize with a target DNA at intervals of about 160 to 400 bases, most preferably about 160 bases. Kits having such a number thus have utility in generating a nested set of deletion fragments separated by about 160–400 bases and in confirming the sequence of mutagenic DNA. For the latter use, a researcher need only select the deletion primer from the kit which should hybridize within a convenient number of bases of the region to be confirmed. The kits may additionally include an inducing agent such as Taq polymerase, the deoxyribonucleoside triphosphates, and any buffers necessary for PCR. The kits may further include the components necessary for the sequencing reactions such as an inducing agent, deoxyribonucleoside and dideoxyribonucleoside triphosphates, and buffers necessary for the sequencing reactions.

The following examples illustrate the invention.

EXAMPLE 1

To verify the utility of the process of the present invention, a known three kilobase DNA fragment that codes for a 99 kd (kilodalton) murine endoplasmic reticulum protein described in Mazzarella et al., J. Biol. Chem., 262:8875–8883 (1987) was used as the target template DNA. The deletion primer oligonucleotides had a six-nucleotide fixed site region, a four-nucleotide spacer region, and a twenty base tail (5′ GTTCGAT-GATTAATTGTCAA 3′).

The sequence of the six-nucleotide fixed base region was determined as follows. Based upon reports that a G-C interaction is stronger than an A-T hybrid, it was determined that fixed site region would have a 50% G-C content and that the two terminal 3′ bases would be a G or a C in order to help "tie-down" the primer to the template DNA. In addition, it was desired to select a sequence which would appear at a statistically satisfactory amount in the target template DNA. In order to accomplish this objective, a random set of known sequenced genes from the rodent library in GenBank were combined and about 161 kilobases of DNA were analyzed for the presence of 72 different six base sequences. These six base sequences all had a G or C at the terminal two positions at the 3′ end and a G or C at either the terminal 5′ end, or one base from the 5′ end. Thus, the structure of the six base sequences were G/C, A/T, A/T, A/T, G/C, G/C or A/T, G/C, A/T, A/T, G/C, G/C. The frequency of these sequences differed significantly. If the DNA in the rodent library were completely random, a six base sequence would be expected to appear 39 times in 161 kilobases (161,000/4096). The range of appearances for the 72 six-base sequences was from 2 to 134. Based upon this information, three six-base sequences GATTCC (sequence #56), ACAAGC (sequence #57) and GAATCC (sequence #58) which appeared 31, 44, and 39 times, respectively, in the 161 kilobase rodent library were selected for evaluation.

The starting materials were prepared, and the amplification and sequencing processes were conducted as follows:

Oligonucleotide Primer Synthesis

Oligonucleotide primers were synthesized on an Applied Biosystems DNA synthesizer according to the manufacturer's instructions. Oligonucleotides were de-blocked with NH4OH overnight at 60° C., dried, and then purified on a 10 ml Sephadex G-50 (medium) column equilibrated with H2O. Fractions (0.5 ml) were collected and a portion of each fraction was analyzed for its optical density at 260 nanometers. The concentration of oligonucleotide was determined by multiplying the O.D. by $7.5 \times 10^{-5}$ and dividing by its length in bases. Fractions were not pooled but instead were used directly.

Target DNA Template Preparation

Because the use of a vector DNA carrying the target DNA can result in artifacts caused by hybridization of the deletion primer with vector DNA, the DNA template used in the PCR reactions was itself a PCR product. The template target DNA was isolated by amplifying the target DNA from the vector using two fixed primers.

In a first approach, these primers hybridized to the 3′ terminus of the LacZ gene 433 bases downstream from the multiple cloning sites in mp18 or mp19 and to a region near the PVU II site located 286 bases upstream from the multiple cloning sites. The sequence for the amplification primers are TAAAAGCTTGCGGT-GAAGGGCAATA and TTAGGATCCTTAAC-CAATAGGAACGCC. Underlined bases are the actual hybridizing bases. Those not underlined are a tail which incorporates the Hind II and Bam HI sites, respectively. These sites were included in the oligonucleotide for unrelated experimental purposes.

In a second approach, the template target DNA was isolated by amplifying the target DNA from the vector using the M13 forward and M13 reverse primers. The M13 forward primer (GTTTTCCCAGTCACGAC) hybridizes 23 bases downstream from the multiple cloning site and the M13 reverse primer (AACAGCTATGACCAGT) hybridizes 5 bases upstream from the multiple cloning site.

The gene cloned in the multiple cloning region was amplified by adding the two amplification primers and performing the PCR reaction as described below except that the hybridization temperature was 52° C. The amplified target DNA was bounded by sites which are complementary to the M13 forward and M13 reverse primers.

Terminus Primers

The M13 forward and M13 reverse primers were used as the terminus primers in the PCR amplification of the deletion fragments. The use of both of these primers in separate reactions enabled the amplification of fragments from opposite strands of the target DNA which extend into the gene from either direction.

Also used as a terminus primer is the ERp99 gene specific primer at position 2620. Its sequence is CTTCCTGTGACCCATAATCCC which is complementary to the coding strand of ERp99.

Preparation of the Nested Set of Deletions using the PCR process

PCR was carried out according to the instructions provided with Taq polymerase sold by Perkin Elmer Cetus (Emeryville, Calif.) except as noted below. The reaction was performed in 50 μL microcentrifuge tubes and the PCR reaction mixtures (50 μl) contained (a) each deoxynucleoside triphosphate (200 μM) neutralized to pH 7.0 with NaOH, (b) a terminus primer (1.0 μM), (c) a set of deletion primers (1.0 μM), (d) target DNA template (5 ng.), (e) Amplitaq ™ DNA polymerase (0.25 units; Cetus), and (f) 1x reaction buffer consisting of 10 mM (millimolar) Tris-HCl (HCl-neutralized Tris (hydroxymethyl)aminomethane) pH 8.2 (at 22° C.), 50 mM KCl, 1.5 mM MgCl₂ and 0.1% BSA (bovine serum albumin). All components of the buffer were autoclaved prior to making a 10x stock buffer except for the BSA, which was sterile filtered. In order to reduce evaporation, the reaction mixture was overlaid with mineral oil (100 μL).

The cycling reaction was done in a DNA thermal cycler sold by Coy (Ann Arbor, Mich.) using the following conditions: 25 cycles of a) denaturation—94° C. for 2 minutes (ramp time of 0.33 minutes), b) hybridization—42° C. for 2 minutes (ramp time 0.33 minutes) and c) polymerization—72° C. for 4 minutes (ramp time of 0.33 minutes). At the end of the final polymerization step a 7 minute polymerization step at 72° C. was performed to ensure complete synthesis of all fragments. After this 7 minute extension the temperature block was automatically cooled to 4° C. and held at that temperature (typically overnight).

Analysis of the PCR Amplified Deletion Fragments

Analysis of the reaction products was performed by first extracting the mineral oil. This was done by adding 100 μL of reagent grade chloroform, briefly vortexing and separating the resulting phases by centrifuging at 10,000 xg in a Hermle microcentrifuge. The aqueous phase containing the DNA floated on the chloroform-oil mixture, and was collected with a piperman tip and placed into a clean microcentrifuge tube. The results of the experiment were analyzed by agarose gel electrophoresis according to Maniatis et al., *Molecular Cloning, A Laboratory Manual*, Cold Spring Harbor Laboratory. Approximately 15 μL of the reactions mix was analyzed by mixing it with 6x sample buffer containing 30% glycerol, 0.25% bromophenol blue and 0.25% xylene cylanol. A 0.8% agarose gel was used to analyze the reactions. All gels used the buffer TAE with a final concentration of 0.5 μg/ml EtBr (ethidium bromide) in both gel and buffer. Standard DNA fragments were electrophoresed in parallel in order to judge the relative size of all fragments. These standards are the Hind III digest of Lambda DNA and the Hae III digest of PhiX 174. Gels were electrophoresed until the bromophenol dye marker was about ⅔ of the way towards the end of the gel.

Sequencing of Deletion Fragments

Sequencing was performed essentially as described by Gorman & Steinberg, (1989) Biotechniques 2:326–329, with minor modification, including the use of the Taq polymerase buffer normally used for DNA amplification (10 mM Tris-HCl pH 8.2 (at 25° C.), 50 mM KCl, 1.5 mM MgCl₂ and 0.01% BSA). Briefly, a two-stage sequencing procedure was used. The DNA fragment to be sequenced was isolated by gel electrophoresis. The band was cut out and not purified any further. All reactions were done in the presence of agarose. The agarose used was GTG seaplaque (FMC), which is a high quality non-inhibitory low melting agarose. Bands were melted at 68° C. for five minutes and up to 4.4 μl was added to the 16 μl reaction mix, containing 1.5 nM each of dCTP, dGTP, and dTTP; 200 nM [a— ³²P]dATP (3000 Ci/Mmol, DuPont-NEN); 0.5–10 pmol oligonucleotide sequencing primer (identical to the deletion primer tail); and 2 units of Amplitaq polymerase. Before adding polymerase, the labeling mix was heated at 94° C. for 7 minutes followed by a 5 minute incubation at 37° C. Amplitaq polymerase was added and the reactions were incubated from 7.5 to 15 minutes at 55° C. 3.5 μl portions were added to 2.5 μl portions of "termination mixes" and incubations were continued at 55° C. for 10 minutes. Reactions were stopped by placing the tubes on ice and freezing the contents at −20° C. overnight. The termination mixes were identical to that described by Gorman & Steinberg. Prior to loading the sequencing gel, 4 μl of a mixture containing deionized formamide with bromophenol blue and xylene cylanol was added to each sample. Sequencing gels were 8% in polyacrylamide and were run at 1500 V in an IBI STS45 apparatus (IBI) soaked in 10% acetic acid, dried onto Whatmann 3MM paper and subjected to autoradiography overnight.

Results

Table I lists the expected deletion fragments that should have been produced. Strand 1 and Strand 2 are the complementary strands from the 3 kilobase target DNA. The numbers identified correspond to the nucleotide position at which the deletion fragment was initiated. The terminus primer for Strand 1 is the M13 forward primer and the terminus primer for Strand 2 is the M13 reverse primer. Fragments underlined were obtained from the PCR reaction, those not underlined were not.

It was verified that the fragments were generated as a result of hybridization of the deletion primer at the correct target site in the template DNA by sequencing the fragment after isolation on a GTG agarose gel as described above. All of the fragments yielded a clean sequence that could be read at about 7 to 15 bases from the primer site. In all cases but one, the fragment generated was due to the expected hybrid between deletion primer and the target DNA template.

In one case, a readable sequence could not be easily obtained. After cleaning up this initially unreadable sequence by using Geneclean, it was possible to generate some readable sequence data. This data showed that the fragment was actually two comigrating fragments. One was generated by the expected hybrid while the other was generated by a hybrid between the five terminal 3′ bases of the deletion primer and a target in the template that was 90 bases away. Further experiments showed that if care was taken to run the gel at lower voltage over a longer path length, the two bands could be separated.

TABLE I

DELETIONS EXPECTED AFTER PCR REACTIONS USING DELETION OLIGONUCLEOTIDES ON THE ENDOPLASMIC RETICULUM PROTEIN ERp99.

| Seq. # | Deletion Primer Fixed Site Region Sequence | Strand 1 | Strand 2 |
|---|---|---|---|
| 56 | GATTCC | 2516, 1781, 803 | 1399 |
| 57 | ACAAGC | 1523 | 2200, 719 |
| 58 | GAATCC | 1445 | 285 |

EXAMPLE 2

Deletion fragments using PCR were prepared and analyzed as set forth in Example 1 except as noted below.

Six sets of deletion primers having different fixed site regions were used. The fixed site regions of the six sets had the sequences AAGAGG (#35), TGGATG (#36), GGAAGA (#48), GATTCC (#56), ACAAGC (#57) and GAATCC (#58), which appear four, seven, nine, four, three, and two times, respectively, in the test gene. Sequences #35, #36 and #48 were not analyzed for their appearance in the 161 kilobase DNA library.

Figure 2:
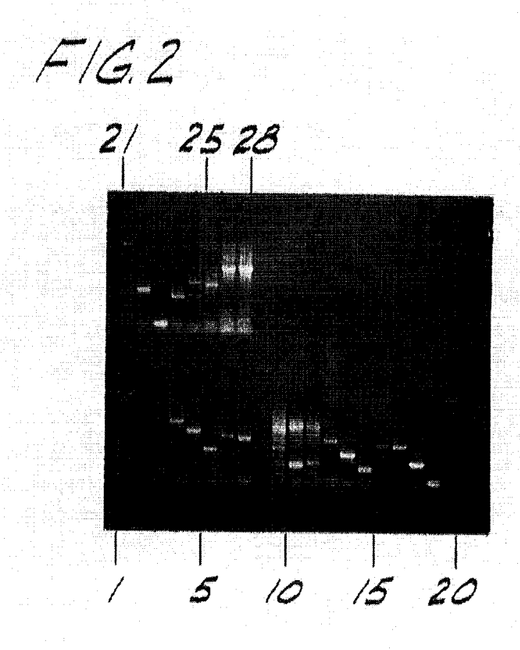
FIG. 2 is a photographic reproduction of an electrophoretic gel described in Example 2.

FIG. 2 shows the pattern of deletions obtained after a typical PCR reaction using sets of deletion primers having these six fixed site regions. Lanes 1, 20 and 21 are DNA standards (see "Analysis of the PCR Amplified Fragments section in Example 1). The terminus primers were used in the reaction mixtures as follows: lanes 2–8, M13 forward primer; lanes 9–15, M13 reverse primer; lanes 16–19, and 22–23 ERp99 gene specific primer at position 2620; and lanes 24–26, M13 forward primer. The sets of deletion primers used in the reaction mixtures had the following fixed site primer sequence numbers: sequence #35 in lanes 3 and 10; sequence #36 in lanes 4 and 11; sequence #48 in lanes 5 and 12; sequence #56 in lanes 6, 13, 17, 22, and 24; sequence #57 in lanes 7, 14, 18 and 25; and sequence #58 in lanes 8, 15, 19, 23 and 26.

For lanes 2–19, the template DNA was derived using the LacZ and Pvu II site primers. For lanes 21–25, the M13 forward and reverse primers were used to generate the template.

As can be seen from Table I and FIG. 2, lane 5, only one of the expected fragments (fragment #2516) using deletion primer #56 was not produced by the PCR reaction. Based on previous work (not outlined) it is believed that this lack of production is related to the six nucleotide positions which would interact with the degenerate spacer region. It appears that if two fragments have about the same percentage G-C to interact with the spacer regions, the smaller PCR fragment will be favored. When the fixed site region of the deletion primer has greater than one target site, the larger fragment must have a more stable hybrid to the spacer region for it to be generated by the PCR reaction. Although this relationship of spacer DNA to target DNA template is not completely defined, the trend appears to be clear.

EXAMPLE 3

Deletion fragments using PCR were prepared and analyzed as set forth in Example 1 except that deletion primers having a seven nucleotide fixed site sequence (GAGGAAG) and two or four nucleotide spacer positions were used.

It was found that the two nucleotide spacer region generated some of the expected fragments whereas a four nucleotide spacer region generated most of the expected fragments.

EXAMPLE 4

Deletion fragments using PCR were prepared and analyzed as set forth in Example 1 except that deletion primers having fixed site primer sequence #56 (GATTCC) and spacer regions of four, six, and ten nucleotides were used.

It was found that the four nucleotide spacer region generated many of the expected fragments. However, a six nucleotide spacer region not only generated most of the expected fragments, but the amount of DNA per fragment was greater than that produced when a four nucleotide spacer region was used. Increasing the length of the spacer region to ten nucleotides did not appear to enhance the number of fragments generated nor did it appear to affect the amount of DNA per band relative to a six nucleotide spacer region.

Based on these results, it is believed that the spacer region of the deletion primer plays a role in binding of the deletion primer to the target DNA template. A good spectrum of fragments begins to appear when the deletion primer has a six nucleotide fixed site region and a four nucleotide spacer region. As shown in Example 3, some fragments also appear when the deletion primer has a seven nucleotide fixed site region and a two nucleotide spacer region. Thus, it appears that the minimum number of bases needed for a stable interaction to occur between the primer and the target DNA template is about nine or ten. The amount of product produced increases when the spacer region has about four or more nucleotide positions.

EXAMPLE 5

Deletion fragments using PCR were prepared and analyzed as set forth in Example 1 except that deletion primers were used having a five nucleotide spacer region and fixed site regions of three, four, and five nucleotides, respectively. The fixed site regions had the following sequences: (AGG), (GAGG), and (AGAGG), respectively.

PCR amplification using sets of deletion primers having a three or four base fixed site region did not produce any DNA fragments.

PCR amplification using sets of deletion primers having a five base fixed site region generated a few of the expected fragments, but not nearly the number expected.

EXAMPLE 6

To verify the utility of the process of the present invention, sets of deletion primers were used in combination with appropriate terminus primers in order to generate a representative set of deletion fragments that covered the entire ERp60 gene, the gene for a 60 kd murine endoplasmic reticulum protein, the sequence of which was unknown.

The template DNA was obtained by PCR amplification of cloned ERp60 DNA in pUC119 which is a derivative of pUC19 and contains the M13 origin at the Nde I site at pUC19 (pUC19 is described in Yanisch-Perron et al., Gene 33:103–119 1985) with the Puu II primer and the Eco RI sequencing primer (New England Biolabs). The ERp60 gene cloned in both orientations in the pUC119.

PCR amplification of the deletion fragments and analysis of the PCR amplified deletion fragments was carried out as set forth in Example 1. The primers used in the PCR amplification step were the M13 forward primer (which served as the terminus primer), and 30 sets of deletion primers having a six nucleotide fixed site region, a six base spacer region, and a twenty base tail (5' GTTCGATGATTAATTGTCAA 3'). Table II identifies the sequences used for the fixed site regions and the lanes in which deletion fragments produced using deletion primers containing such sequences were analyzed.

It should be noted that the M13 forward primer is about 1000 bases from the Eco RI primer. Thus, the largest fragment that could be generated using the deletion primers and the M13 forward primer is about 1000 bases less than the original template.

Figure 3:
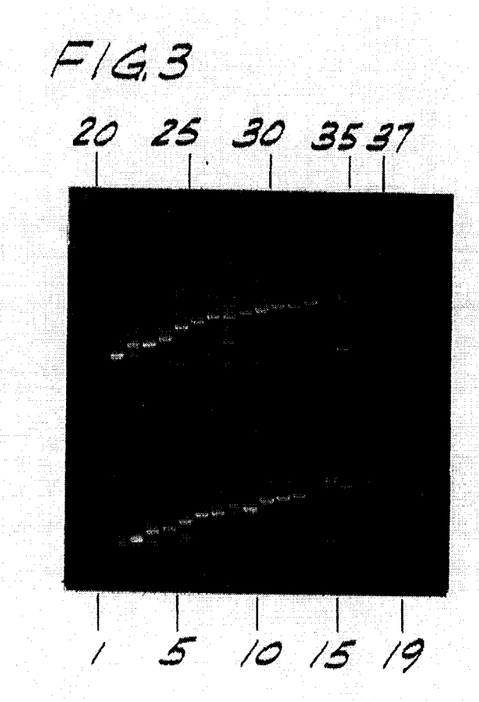
FIG. 3 is a photographic reproduction of an electrophoretic gel described in Example 6.

After initial analysis by agarose gel electrophoresis, the nested set shown in FIG. 3 was compiled. In some instances, the bands shown were not generated from the initial PCR reaction but were obtained by reamplification of an agarose gel purified fragment. Fragments obtained by such reamplification are in lanes 2, 3, 4, 6, 7, 8, 9, 10, 15, 21, 22, 23, 24, 25, 27, 28, and 35; the remaining lanes are fragments obtained in the initial PCR reaction.

Because the ERp60 cloned in both orientations, the strand used in the deletions depended upon which original orientation the gene was found in pUC119. Fragments generated from the two strands are separated and shown in separate panels in FIG. 3 with all of the fragments in the upper panel being generated from one strand and with all of the fragments in the lower panel being generated from the other strand. Lanes 1, 19, 20 and 37 were produced using the standards of Example 1. Lanes 18 and 36 were produced using the original template DNA obtained from the ERp60 cloned in different orientation in the pUC119.

In some lanes, more than one band is seen because the deletion primer hybridized at more than one site on the template strand. Purification by agarose gel electrophoresis of higher molecular weight fragments and subsequent reamplification usually does not yield a pure band; the higher molecular weight bands often contain contaminating lower molecular weight fragments.

Sequencing information concerning the ERp60 gene could be obtained by performing sequencing reactions on the generated nested set of fragments as set forth in Example 1 and compiling the resulting information.

TABLE II

| Lane | Sequence of 3' fixed end of deletion oligonucleotide |
|---|---|
| 2 | CAATGC |
| 3 | TGTAGC |
| 4 | CATTCC |
| 5 | GTCCAA |
| 6 | CAATGC |
| 7 | CATGAT |
| 8 | GAAGAT |
| 9 | TGTAGC |
| 10 | CATGAT |
| 11 | GTTTCC |
| 12 | CAAAAC |
| 13 | CTTTGC |
| 14 | GAATGG |
| 15 | CATTCC |
| 16 | CAAAAG |
| 17 | TGTAGG |
| 21 | TGTAGC |
| 22 | TGTAGC |
| 23 | TGTAGG |
| 24 | CATGAT |
| 25 | GAAGAT |
| 26 | CTATGC |
| 27 | GTGGAT |
| 28 | GTCCAA |
| 29 | GAATGG |
| 30 | CCAACA |
| 31 | ACATGC |
| 32 | GTTTCC |
| 33 | GAATCC |
| 34 | TGTAGG |
| 35 | TGTAGG |

In view of the above, it will be seen that the several objects of the invention are achieved and other advantageous results attained.

As various changes could be made in the above processes and products without departing from the scope of the invention, it is intended that all matter contained in the above description shall be interpreted as illustrative and not in a limiting sense.

What is claimed:

1. A process for the preparation of a deletion fragment from a target nucleic acid, the target having a region of known nucleotide sequence identical to one terminus of the deletion fragment, the process comprising:

(a) providing the target nucleic acid as a single stranded molecule, (b) providing a terminus primer which is homologous to the region of known nucleotide sequence, (c) providing a set of deletion primers having a fixed site region at the 3' end thereof, a tail at the 5' end thereof, and a spacer region comprising N consecutive nucleotide positions wherein N is at least two between the fixed site region and the tail, the set of deletion primers comprising a mixture of about $4^N$ oligonucleotides having homologous fixed site regions and homologous tails, and collectively having each of the four bases at each nucleotide position of the spacer region, (d) treating the single strands with the terminus primer and the set of deletion primers to form a primer extension product wherein the target nucleic acid is used as a template, (e) separating the primer extension product from the template on which it was synthesized to produce single stranded molecules, and (f) treating the single stranded molecules generated in step (e) with the primers of steps (b) and (c) to form a primer extension product wherein the single strands produced in step (e) are used as a template.

2. The process of claim 1 wherein the tail is substantially non-complementary to the target nucleic acid.

3. The process of claim 1 wherein N is at least 4.

4. The process of claim 2 wherein the fixed site and spacer regions of the oligonucleotides comprising the deletion primers collectively have at least about nine nucleotides.

5. The process of claim 1 wherein the deletion primers have a combined total of at least twelve nucleotides in their fixed site and spacer regions.

6. The process of claim 3 wherein the deletion primers have a fixed site region comprising at least five nucleotides.

7. The process of claim 1 wherein N is at least six.

8. The process of claim 1 wherein steps (e) and (f) are repeated at least once.

9. The process of claim 1 wherein steps (d) and (f) are carried out at a temperature of about 42° C.

10. The process of claim 1 wherein steps (d) and (f) are carried out at a temperature of less than about 52° C.

11. The process of claim 1 wherein said process additionally comprises the step of sequencing the primer extension products of step (f).

12. The process of claim 1 wherein the single strands are treated in step (d) with Taq polymerase.

13. A process for the preparation of a nested set of deletion fragments from a target nucleic acid, the target having a region of known nucleotide sequence identical to one terminus of the deletion fragment, the process comprising:

(a) providing the target nucleic acid as a single stranded molecule, (b) providing a terminus primer which is homologous to the region of known nucleotide sequence, (c) providing a plurality of sets of deletion primers having a fixed site region at the 3' end thereof, a tail at the 5' end thereof, and a spacer region between the fixed site region and the tail, the spacer region comprising N consecutive nucleotide positions wherein N is at least two, each set of deletion primers comprising a mixture of oligonucleotides which collectively have all four bases at each nucleotide position in a plurality of combinations thereof in their spacer regions, distinct sets of primers differing from one another with respect to the sequence of bases which comprise the fixed site regions of their respective mixtures, the tails being substantially non-complementary to the target nucleic acid, (d) dividing the target nucleic acid into separate aliquots, (e) treating the aliquots with the terminus primer and with different sets of deletion primers to form a primer extension product wherein the target nucleic acid is used as a template, (f) for each aliquot, separating the primer extension product from the template on which it was synthesized to produce single stranded molecules, and (g) for each aliquot, treating the single stranded molecules generated in step (f) with the primers of steps (b) and (c) to form a primer extension product wherein the single strands produced in step (f) are used as a template.

14. The process of claim 13 wherein the fixed site and spacer regions of the oligonucleotides comprising the deletion primers have a combined total of at least ten nucleotides.

15. The process of claim 13 wherein the sets of oligonucleotides comprising the deletion primers have fixed site and spacer regions which have a combined total of at least twelve nucleotides.

16. The process of claim 13 wherein the fixed site region of the oligonucleotides comprising the deletion primers have at least five nucleotides.

17. The process of claim 13 wherein each set of deletion primers is a mixture of about $4^N$ oligonucleotides wherein N equals the number of nucleotide positions comprising the spacer region of the deletion primers.

18. The process of claim 13 wherein the oligonucleotides comprising the deletion primers have at least about six nucleotides in their fixed site regions.

19. The process of claim 13 wherein steps (f) and (g) are repeated at least twice.

20. The process of claim 13 wherein steps (e) and (g) are carried out at a temperature of about 42° C.

21. The process of claim 13 wherein steps (e) and (g) are carried out at a temperature of less than about 52° C.

22. The process of claim 13 wherein the process additionally comprises the step of sequencing the primer extension products of step (g).

23. The process of claim 13 wherein said plurality of sets is at least twenty-five sets.

24. The process of claim 13 wherein the different sequences of the fixed site regions of the oligonucleotides comprising the deletion primers are selected based on a mathematical probability that the fragments produced therefrom will not be separated by more than about 400 bases.

25. A kit for the preparation of a nested set of deletion fragments from a target nucleic acid, the target having a region of known nucleotide sequence identical to one terminus of the deletion fragment, the kit comprising a plurality of sets of deletion primers having a fixed site region at the 3' end thereof, a tail at the 5' end thereof, and a spacer region between the fixed site region and the tail, the spacer region comprising N consecutive nucleotide positions wherein N is at least two, each set of deletion primers comprising a mixture of about $4^N$ oligonucleotides which collectively have all four bases at each nucleotide position in a plurality of combinations thereof in their spacer regions, distinct sets of primers differing from one another with respect to the sequence of bases which comprise the fixed site regions of their respective mixtures.

26. The kit of claim 25 additionally comprising a terminus primer which is homologous to the region of known nucleotide sequence.

27. The kit of claim 25 additionally comprising an inducing agent comprising Taq polymerase.

28. The kit of claim 25 wherein the fixed site and spacer regions of the oligonucleotides comprising the deletion primers collectively have a combined total of at least nine nucleotides.

29. The kit of claim 25 wherein the deletion primers have a combined total of at least about twelve nucleotides in their fixed site and spacer regions.

30. The kit of claim 25 wherein the deletion primers have a fixed site region comprising at least six nucleotides.

31. The kit of claim 25 wherein the deletion primers comprise a spacer region having at least about four nucleotides.

32. The kit of claim 25 wherein said plurality of sets is at least twenty-five sets.

33. A mixture of oligonucleotide primers having a fixed site region at the 3' end thereof, a tail at the 5' end thereof, and a spacer region between the fixed site region and the tail, the spacer region comprising N consecutive nucleotide positions wherein N is at least two, the oligonucleotides having homologous fixed site regions and homologous tails, the mixture collectively having all four bases at each nucleotide position in a plurality of combinations thereof in the spacer region.

34. The mixture of claim 33 wherein the mixture contains about $4^N$ oligonucleotides wherein N equals the number of nucleotide positions comprising the spacer region of the oligonucleotide primers.

35. The mixture of claim 33 wherein the fixed site and spacer regions of the oligonucleotides have a combined total of at least nine nucleotides.

36. The mixture of claim 33 wherein the oligonucleotides have a combined total of at least twelve nucleotides in their fixed site and spacer regions.

37. The mixture of claim 33 wherein the oligonucleotides have a fixed site region comprising at least six nucleotides.

* * * * *

UNITED STATES PATENT AND TRADEMARK OFFICE
CERTIFICATE OF CORRECTION

PATENT NO. : 5,407,813
DATED : April 18, 1995
INVENTOR(S) : Paul Gold

It is certified that error appears in the above-indentified patent and that said Letters Patent is hereby corrected as shown below:

Column 17:
    In claim 13, line 44, after "oligonucleotides" insert -- which have homologous fixed site regions and homologous tails, and --.

Column 18:
    In claim 25, line 45, after "oligonucleotides" insert -- which have homologous fixed site regions and homologous tails, and --.

Signed and Sealed this

Eighteenth Day of March, 1997

Attest:

BRUCE LEHMAN

Attesting Officer    Commissioner of Patents and Trademarks